United States Patent [19]

Payne et al.

[11] 4,356,023

[45] Oct. 26, 1982

[54] CERTAIN HERBICIDAL TETRAHYDROFURANS

[75] Inventors: George B. Payne; Samuel B. Soloway, both of Modesto, Calif.

[73] Assignee: Shell Oil Company, Houston, Tex.

[21] Appl. No.: 164,209

[22] Filed: Jun. 30, 1980

[51] Int. Cl.$^3$ .................. A01N 43/08; C07D 307/12
[52] U.S. Cl. .......................................... 71/88; 549/502
[58] Field of Search .......................... 71/88; 260/347.8

[56] References Cited

U.S. PATENT DOCUMENTS

| 3,466,304 | 9/1969 | Elliot et al. | 260/347.8 |
| 4,070,381 | 1/1978 | Van der Ouweland | 260/347.8 |
| 4,116,669 | 9/1978 | Barker et al. | 71/88 |
| 4,146,384 | 3/1979 | Schmidt et al. | 71/88 |

FOREIGN PATENT DOCUMENTS 2724675  12/1978  Fed. Rep. of Germany .
2724677  12/1978  Fed. Rep. of Germany .

OTHER PUBLICATIONS

Fukuyamo et al., Chem. Abst. vol. 90, (1979), 87152f.
Knollmann et al., Chem. Abst. vol. 87, (1977), 168304x.

*Primary Examiner*—Catherine L. Mills

[57] ABSTRACT

Certain substituted tetrahydrofurans, and their use for controlling unwanted plants.

3 Claims, No Drawings

CERTAIN HERBICIDAL TETRAHYDROFURANS

DESCRIPTION OF THE INVENTION

It has been found that useful herbicidal properties are exhibited by three tetrahydrofurans described by the formula:

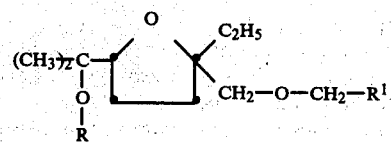

wherein R and $R^1$ have certain meanings.

The compounds of Formula I contain three chiral centers. The isomers have not been isolated. This invention contemplates all of the herbicidally active isomers, as well as mixtures containing them.

The three compounds are the individual species of the class defined by Formula I wherein the substituent moieties, R and $R^1$, are as follows:

| Compound No. | R | $R^1$ |
|---|---|---|
| 1 | hydrogen | phenyl |
| 2 | methyl | phenyl |
| 3 | methyl | 2-fluorophenyl |

These compounds can be prepared as described in the examples. In each case, the identity of the product and of each intermediate was confirmed by appropriate elemental and spectral analyses.

EXAMPLE 1

5-ethyltetrahydro-α,α-dimethyl-5-((phenylmethoxy)-methyl)-2-furanmethanol (1)

42.8 g of 85% meta-chloroperbenzoic acid was added in portions to a stirred solution of 13.6 g of myrcene in 300 ml of methylene chloride at $-20°$ to $-15°$ C. The resulting mixture was allowed to warm slowly (over a period of one hour) to 5° C. and was held there overnight. The mixture then was filtered. The filtrate was washed with one-fourth saturated potassium carbonate solution, dried over magnesium sulfate, concentrated and Claisen-distilled to give an approximately 80:20 mixture (1A) of the stereoisomeric forms of 3-(2(2-ethenyl-2-oxiranyl)ethyl)-2,2-dimethyl-oxirane, a liquid, bp: 74°–76° C. (3 Torr.).

A mixture of 5.1 g of 1A and 100 ml of 1 N sodium hydroxide was stirred vigorously at reflux for 20 minutes, then cooled rapidly to room temperature and extracted with methylene chloride. The extract was dried and Claisen-distilled (micro) to give an approximately 90:10 mixture of the stereoisomeric forms (1B) of 2-ethenyltetrahydro-alpha$^5$,-alpha$^5$-dimethyl-2,5-furandimethanol, a viscous, colorless liquid.

A mixture of 8.9 g of 1B, 75 ml of ethanol (containing 5% toluene) and 1.2 g of palladium-on-barium sulfate catalyst was shaken in a Parr hydrogenator at an initial hydrogen pressure of 56 p.s.i.g. Within 30 minutes, hydrogen uptake ceased at 40 pounds absorption (bottle only). The resulting mixture was filtered and the filtrate was Claisen-distilled to give 2-ethyltetrahydro-alpha$^5$,alpha$^5$-dimethyl-2,5-furandimethanol (1C) as a viscous colorless liquid, bp: ca 90° C. (0.1 Torr.).

1.8 g of 50% sodium hydride (previously washed with hexane) was added in portions to a stirred solution of 7.1 g of 1C in 75 ml of N,N-dimethylacetamide, with cooling to moderate the mildly exothermic reaction. After one hour, 4.8 g of benzyl chloride was added. The mixture was stirred overnight at 25° C., poured into water and extracted with methylene chloride. The extract was washed with water, dried, concentrated and Claisen-distilled to give 1, as a liquid, bp: 110°–112° C. (0.1 Torr.).

EXAMPLE 2

2-ethyltetrahydro-4-(1-methoxy-1-methylethyl)-2-((phenylmethoxy)methyl)furan (2)

A mixture of 2.8 g of 1, 25 ml of N,N-dimethylacetamide and 0.6 g of 50% sodium hydride (washed) was stirred at 45°–50° C. for 2 hours, and then treated with 2 ml of methyl iodide. The mixture then was stirred for 2 hours, at 45°–50° C., cooled, poured into water, and extracted with methylene chloride. The extract was washed with water, dried, concentrated and distilled to give 2, as a liquid, bp: ca 100° C. (0.1 Torr.).

EXAMPLE 3

2-Ethyl-2-((2-fluorophenylmethoxy)methyl)tetrahydro-5-(1-methoxy-1-methylethyl)furan (3)

3 was synthesized from 1C, using 2-fluorobenzyl chloride, instead of benzyl chloride, in the same manner as described for 1.

The compounds of Formula I have been found to be useful for killing unwanted plants, being active with respect to both broad-leaved plants and grasses, being more active when applied preemergence (applied to the soil before the plants have sprouted) than when applied postemergence (to the foliage of the plants).

Accordingly, the invention includes a method of killing unwanted plants which comprises applying to the locus an effective amount of a compound of Formula I. Likewise the invention also includes herbicidal compositions comprising a carrier or a surface-active agent, or both a carrier and a surface-active agent, and, as active ingredient at least one compound of Formula I.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates, for example, natural silicas such as diatomaceous earths; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquefied normally vaporous gaseous compounds. Mixtures of different liquids are often suitable. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3-10% by weight of a dispersing agent, 15% of a surface-active agent and where necessary, 0-10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½-10% by weight of toxicant. Granules are usually prepared to have a size between 10 and 100 BS mesh (1.676-0.152 mm), and may be manufactured by agglomeration or impregnation techniques. Generally, granules will contain ½-25% by toxicant and 0-1% by weight of additives such as stabilizers, slow release modifiers and binding agents. Emulsifiable concentrates usually contain, in addition to the solvent and, when necessary, cosolvent, 10-50% weight per volume toxicant, 2-20% weight per volume emulsifiers and 0-20% weight per volume of appropriate additives such as stabilizers, penetrants and corrosion inhibitors. Suspension concentrates are compounded so as to obtain a stable, nonsedimenting, flowable product and usually contain 10-75% weight toxicant, 0.5-5% weight of dispersing agents, 1-5% of surface-active agent, 0.1-10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

Protection of a locus or area from undesirable plants is effected by applying a compound of Formula I, ordinarily in a composition of one of the aforementioned types, to the foliage of the plants or plant growth medium, e.g., soil in which the plant is growing or in which the seeds are present. The active compound, of course, is applied in an amount sufficient to exert the desired action.

The amount of compound of the invention to be used in controlling undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kilograms per hectare of the compound of Formula I will be satisfactory.

Examples of Herbicidal Activity

The preemergence herbicidal activity of the compounds of the invention was evaluated by planting seeds of watergrass (*Echinochloa crus-galli*), garden cress (*Lepidium sativum*), downy brome (*Bromus tectorum*), velvetleaf (*Abutilon theophrasti*), yellow foxtail (*Setaria lutescens*), and sicklepod (*Cassia obtusifolia*) in test tubes, nominally measuring 25×200 millimeters, filled about three-quarters full of untreated soil, in each case covered on top with about 2.5 cubic centimeters of soil treated with the test compound at the rate of 0.1 and 1 milligram per tube, designated in Table I at Rates I and II, respectively. The dosages of test compound were approximately two and twenty pounds of test compound per acre, respectively. The seeds were planted in the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
| --- | --- |
| 9 | No living tissue |
| 8 | Living tissue, but plant expected to die |
| 7 | Plant badly damaged, but expected to live |
| 6 | Plant badly damaged, but expected to recover completely |
| 5 | Unacceptable damage for crop plants, insufficient damage to weeds |
| 3-4 | Definite damage |
| 1-2 | Plant slightly affected, possibly by the chemical, possibly due to biological variability |
| 0 | No visible effect |

The postemergence activity of the compounds of this invention was evaluated by spraying 10-day old large crabgrass (*Digitaria sanguinalis*) plants, 13-day old redroot pigweed (*Amaranthus retroflexus*) plants, 6-day old Johnsongrass (*Sorghum halopense*) plants, 9-day old velvetleaf plants, 9-day old yellow foxtail plants and 9-day old sicklepod plants to runoff with a liquid formulation of the test compound at the rates of 2.4 milliliters of a 0.025% solution (about one pound of Compound I per acre), designated Rate I in Table I, and 2.4 milliliters of a 0.25% solution (about ten pounds of Compound I per acre), designated Rate II in Table I. The sprayed plants were held under controlled conditions of temperature, moisture and light for 7 to 8 days and the effect of Compound I was then evaluated visually, the results being rated on the 0 to 9 scale described above.

The results of the tests are summarized in Table I.

TABLE I
HERBICIDE SCREEN RESULTS

| | Preemergence (Soil) | | | | | | | | | | | | Postemergence (Foliar) | | | | | | | | | | | |
|---|---|---|---|---|---|---|---|---|---|---|---|---|---|---|---|---|---|---|---|---|---|---|---|---|
| | Water Grass | | Garden Cress | | Downy Brome | | Velvetleaf | | Yellow Foxtail | | Sicklepod | | Crabgrass | | Pigweed | | Johnsongrass | | Velvetleaf | | Yellow Foxtail | | Sicklepod | |
| Compound | I | II | I | II | I | II | I | II | I | II | I | II | I | II | I | II | I | II | I | II | I | II | I | II |
| 1 | 8 | 9 | 0 | 4 | 8 | 9 | 0 | 2 | — | — | — | — | 2 | 8 | 2 | 3 | — | — | — | — | 2 | 6 | 2 | 6 |
| 2 | 8 | 8 | 0 | 9 | 9 | 9 | 3 | 3 | 8 | 9 | 0 | 6 | 6 | 8 | 3 | 6 | — | — | — | — | 3 | 8 | 2 | 6 |
| 3 | 9 | 9 | 3 | 3 | 9 | 9 | 4 | 5 | 9 | 9 | 4 | 6 | 6 | 8 | 0 | 6 | 7 | 8 | 0 | 6 | 8 | 8 | 3 | 8 |

We claim:

1. 5-Ethyltetrahydro-$\alpha,\alpha$-dimethyl-5-((phenylmethoxy)methyl)-2-furanmethanol.

2. A herbicidal composition comprising a herbicidal amount of the compound of claim 1, and at least one surface-active agent or carrier therefor.

3. A method for killing unwanted plants at a locus which comprises applying to the locus to be protected a herbicidal amount of the compound of claim 1 or a composition containing it.

* * * * *